United States Patent
Shen et al.

(10) Patent No.: US 8,449,919 B2
(45) Date of Patent: May 28, 2013

(54) COMPOSITION AND METHOD FOR PREPARING ALGINATE NANOCAPSULES

(76) Inventors: Bingqian Shen, Shanghai (CN); Shengli Yang, Shanghai (CN)

( * ) Notice: Subject to any disclaimer, the term of this patent is extended or adjusted under 35 U.S.C. 154(b) by 1048 days.

(21) Appl. No.: 11/368,743

(22) Filed: Mar. 6, 2006

(65) Prior Publication Data

US 2007/0202183 A1    Aug. 30, 2007

(30) Foreign Application Priority Data

Feb. 24, 2006 (CN) .......................... 2006 1 0024132

(51) Int. Cl.
*A61K 9/50* (2006.01)
*B29C 39/10* (2006.01)

(52) U.S. Cl.
USPC ................................. 424/490; 264/4; 977/906

(58) Field of Classification Search
None
See application file for complete search history.

(56) References Cited

U.S. PATENT DOCUMENTS

| 4,352,883 | A |   | 10/1982 | Lim |   |
|---|---|---|---|---|---|
| 4,822,534 | A | * | 4/1989 | Lencki et al. | 264/4.3 |
| 5,674,495 | A |   | 10/1997 | Bowersock |   |
| 6,749,868 | B1 | * | 6/2004 | Desai et al. | 424/491 |

FOREIGN PATENT DOCUMENTS

SU    1432064    10/1988

OTHER PUBLICATIONS

Reis et al, Nanomedicine, Nanoencapsulation I, 2 , 2006, p. 8.*
Hodson, Journal of controlled Release, 33, 1995, p. 143.*
Smidsrod et al., Alginate as immboilization matrix for cells, TIBTECH, Elsevier Science Publishers Limited (UK), Mar. 1990 vol. 8.
Reis et al., Nanoparticulate delivery system for insulin: Design, characterization and in vitro/in vivo bioactivity, European Journal of Pharmaceutical Sciences, Elsevier B.V., 30 (2007) 392-397.
Reis, et al., Design of Insulin-Loaded Alginate Nanoparticles: Influence of the Calcium on Polymner Gel Matrix Properties, CI&CEQ 12 (1) 45-52 (2006).
Shen et al., Calcium alginate immobilized hybridomas grown using a fluidized-bed perfusion system with a protein-free medium, Cytotechnology, 14:109-117,1994.
Shen et al., Hybridoma cells in a protein-free medium within a composite gel perfusion bioreactor, Cytotechnology 16:51-58,1994.
Abraham et al., Novel Technology for the Preparation of Sterile Alginate-poly-l-lysine Microcapsules in a Bioreactor, Pharmaceutical Development &Technology 1(1):63-68, 1999.
Monshipouri et al., Emulsification preparation of calcium alginate beads in the presence of sequesterant, J. Microencapsulation 12 (3): 255-262, 1995.
Wan et al., Drug encapsulation in alginate microspheres by emulsification, J. Microencapsulation 9 (3): 309-316, 1992.
McHugh, Alginate production methods, A guide to the seaweed industry, FAO Fisheries Technical Paper 441, (2003) http://www.fao.org/docrep/006/y4765e/y4765e08.htm.
Haug et al., The Solubility of Alginate at Low pH, Norwegian Institute of Seaweed Research, Acta Chem. Scand. 17 (1963) No. 6.

\* cited by examiner

*Primary Examiner* — David J Blanchard
*Assistant Examiner* — Thurman Wheeler
(74) *Attorney, Agent, or Firm* — Quarles & Brady, LLP

(57) ABSTRACT

The present invention discloses a method for preparing alginate nanocapsules, including the steps of: (a) forming a water-in-oil emulsion including an alginate in water, an oil, and at least one nonionic surfactant; and (b) separating the aqueous phase and oil phase to obtain the semisolid form alginate nanocapsules; and (c) by ionically crosslinking the alginate with calcium ions to obtain a colloidal form of calcium alginate nanocapsules for drug delivery.

11 Claims, 3 Drawing Sheets

COMPOSITION AND METHOD FOR PREPARING ALGINATE NANOCAPSULES

BACKGROUND OF THE PRESENT INVENTION

1. Field of Invention

The present invention relates to compositions of alginate nanocapsules and methods for preparing thereof, and more particularly, relates to compositions and methods for preparing alginate nanocapsules as carriers for the delivery of drugs and macromolecules in non-parenteral, parenteral, oral, and inhalation therapy as well as tools in other biomedical applications.

2. Description of Related Arts

Alginate is used extensively as a mold-making material in dentistry and prosthetics, and in textiles. It is also used in the food industry for thickening soups and jellies. Chemically, alginate is a type of polysaccharides isolated from brown algae. It is a linear copolymer with homopolymeric blocks of guluronic (G) and mannuronic (M) acids as G blocks, M blocks and guluronic-mannuronic (G-M) alternating sequences. Among these three types of structural elements, only G blocks are involved in the gelation of alginate by reacting with multiple cations such as $Ca^{2+}$ and $Ba^{2+}$.

The monomers can appear in homopolymeric blocks of consecutive G-residues (G-blocks), consecutive M-residues (M-blocks), alternating M and G-residues (G-M blocks) or randomly organized blocks. The relative amount of each block type varies with the origin of the alginate. Alternating blocks form the most flexible chains and are more soluble at lower pH than the other blocks. G-blocks form stiff chain elements, and two G-blocks of more than 6 residues each can form ionically cross-linked junctions with divalent cations e.g. $Ca^{2+}$, $Ba^{2+}$, $Sr^{2+}$ among others, leading to a three-dimensional gel network. In these ionically cross-linked gels, it is mostly the homopolymeric G blocks that form the junctions, where the stability of the gel is determined by the relative amount of divalent cations combined.

There exists a free carboxyl group on each of the guluronic or mannuronic moiety. When these carboxyl groups are not ionized, e.g. in a low pH aqueous environment, alginate molecules are not hydrated and become insoluble. However, alginate molecules become soluble and fully hydrated when the pH is neutral or alkaline. Under this condition, the reaction between G blocks and cations such as $Ca^{2+}$ and $Ba^{2+}$ leads to the ionic gelation of alginate. Encapsulation or containment of active ingredients is realized once alginate polymers complete phase transition from a liquid to a solid gel.

U.S. Pat. No. 4,352,883 discloses the use of alginate in preparing semipermeable capsules for the encapsulation of biological materials such as pancreatic islets and mammalian cells. Microcapsules served to isolate the cells from immunological responses of the host while transplanted tissues or cells secreting biological molecules in order to correct abnormal physiological conditions as the case of insulin secreted by β cells in the metabolic disease of Type I diabetes. Shen et al. developed fluidized-bed perfusion bioreactors with hybridoma cells encapsulated in calcium alginate (Cytotechnology, 14:109-117, 1994) and a composite gel beads (Cytotechnology 16: 51-58, 1994) as an effort to increase cell densities and productivities of bioreactors manufacturing biologicals such as monoclonal antibodies. However, these applications required capsules relatively large, 100-2,500 µm in diameter, for reasons either the sizes of tissues to be encapsulated or the operational requirement of the bioreactor systems.

Abraham et al. (Pharmaceutical Development & Technology 1(1): 63-68, 1996) used the Turbotek Atomization technique in a closed system and generated calcium alginate beads of 2.6-7.8 (NWMD) or 4.8-17.2 µm (VWMD) in diameter.

U.S. Pat. No. 4,822,534 discloses a method for producing alginate microspheres of 20-800 µm in diameter by introducing insoluble calcium salt (citrate) to alginate, emulsifying in a hydrophobic liquid and adding oil soluble acid (acetic acid) to allow calcium ions to be released and cause the alginate to gel. Monshipouri and Price used a similar strategy and produced calcium alginate capsules of 50-200 µm in diameter (J. Microencapsulation 12 (3): 255-262, 1995).

Wen et al. emulsified alginate solution in isooctane (J. Microencapsulation 9 (3): 309-316, 1992) first and then added calcium chloride solution to the emulsion. The calcium alginate capsules thus produced were up to 150 µm in diameter. In a similar way, U.S. Pat. No. 5,674,495 claims an oral vaccine composition of antigens in calcium alginate capsules, sizing from 1-30 µm in diameter, prepared by adding calcium chloride solution to emulsion of alginate containing antigens.

U.S. Pat. No. 1,432,064 discloses a process of making calcium alginate by reacting emulsion of alginate with the microemulsion of calcium chloride, to produce capsules of alginate. However, there is no information disclosed about the size and physical properties of gels.

Conclusively, to encapsulate biologically active ingredients within alginate capsules, it is critical to realize the completion of the phase transformation of alginate from a liquid to a solid gel. Conventionally, such phase transformation is processed by reacting liquid droplets of alginate made by extrusion, atomization or emulsion with the ionic crosslinking solution or emulsion of ionic crosslinking solution such as calcium chloride. All these methods used the same mechanism that the moieties of alginate contact directly with ionic crosslinking solution or emulsions of ionic crosslinking solution. However, the ionic crosslinking solution or emulsions of ionic crosslinking solution would be rather costly in practices.

On the other hand, in conventional emulsion approach, gelation of alginate starts after the collision and fusion between the droplets of alginate and ionic crosslinking solution. Thus it is unavoidable to introduce cavities on the alginate capsules formed or cause variations of the alginate capsules from spherical shape such as hemispherical particles.

As a result, to effectively deliver biologically active ingredients, it is believed that there is a need to develop new method to prepare alginate capsules smaller than 1 µm, wherein the complicated crosslinking procedure could be optionally chosen in applications.

SUMMARY OF THE PRESENT INVENTION

A primary object of the present invention is to provide a composition and method for making, using and preserving alginate nanocapsules as carriers for the delivery of drugs and macromolecules in non-parenteral, parenteral, oral, and inhalation therapy as well as tools in other biomedical applications, wherein the nanocapsule has a size smaller than 1 µm while maintaining spherical shape.

Another object of the present invention is to provide a method for preparing alginate nanocapsules, wherein phase transformation of alginate is accomplished by introducing into a state of semisolid of alginate.

Another object of the present invention is to provide a method for preparing alginate nanocapsules, wherein a state of semisolid of alginate is created by introducing an organic acid in both phases after the formation of alginate microemulsion.

Another object of the present invention is to provide a process for preparing alginate nanocapsules, wherein the organic acid diffuses into the droplets of aqueous phase from the oil phase and neutralizes the ionized carboxyl groups, causing alginate to become insoluble while maintaining spherical shape.

Another object of the present invention is to provide a process for preparing alginate nanocapsules, wherein the ionic crosslinking solution or emulsions of ionic crosslinking solution, such as calcium chloride would be optionally required, as a result, there is no possibilities that collision and fusion between the droplets of alginate and ionic crosslinking solution, the capsules are formed without cavities or variations from spherical shape.

Accordingly, to achieve above mentioned objects, the present invention provides a composition and a method of preparation including the following steps:
 a. Adding alginate solution into methylene chloride to form an alginate microemulsion;
 b. centrifuging the alginate microemulsion to separate an aqueous phase semisolid form alginate nanocapsules and an oil phase; and
 c. treating the aqueous phase semisolid form to obtain alginate capsules.

These and other objectives, features, and advantages of the present invention will become apparent from the following detailed description, the accompanying drawings, and the appended claims.

DETAILED DESCRIPTION OF THE PREFERRED EMBODIMENT

Figure 1:
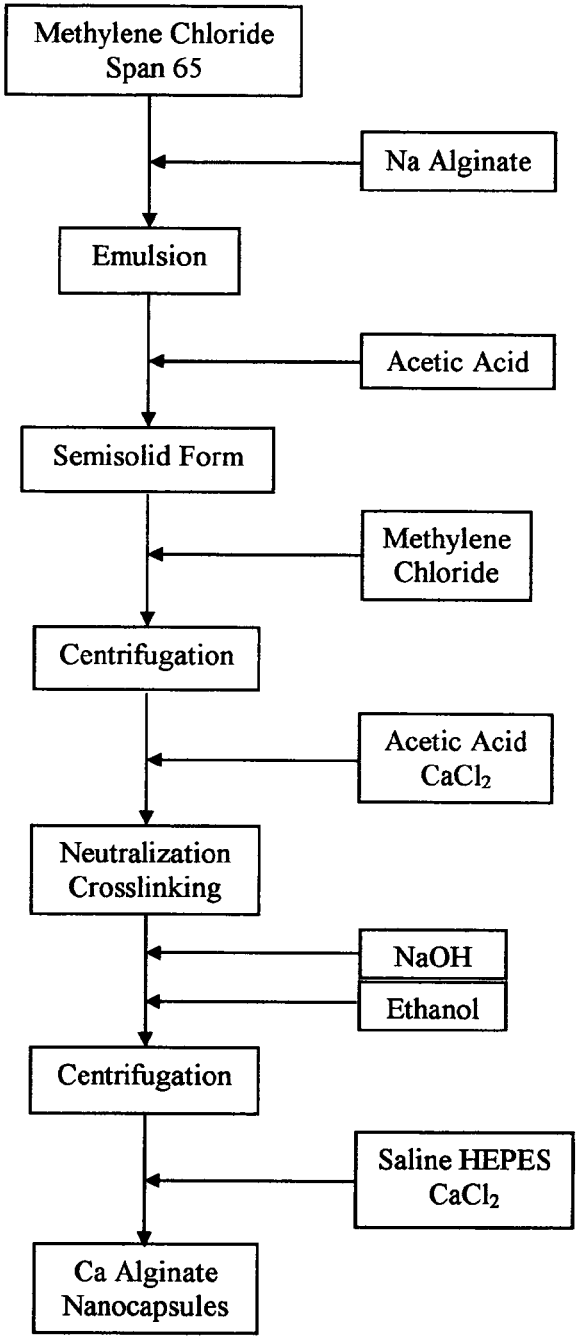
FIG. 1 is a flowchart showing the method for preparing alginate nanocapsules according to a preferred embodiment of the present invention.

Referring to FIG. 1, a method for preparing alginate nanocapsules according to the preferred embodiment of the present invention is illustrated; the method comprises the following steps:
 a. Adding alginate solution into methylene chloride to form an alginate microemulsion;
 b. centrifuging the alginate microemulsion to separate an aqueous phase semisolid form alginate nanocapsules and an oil phase; and
 c. treating the aqueous phase semisolid form to harvest alginate capsules.

Accordingly, the invention provides a composition and a method of preparation including the steps of: (a) forming a water-in-oil emulsion including an alginate in water, an oil, and at least one nonionic surfactant; and (b) separating the aqueous phase and oil phase; and (c) a step by ionic crosslinking the alginate in the aqueous phase with calcium ions to cause alginate to gel.

In step (a), aqueous sodium alginate solution (1% (w/v) in 10 mM HEPES, pH 7.4) is added to organic solvent methylene chloride containing non-ionic surfactant Span 65. With gentle shaking and inversion, mineral oil is added until the densities are balanced between the oil and aqueous phase. A w/o microemulsion is formed with the help of sonication on an ice bath.

Furthermore, the step (b) comprises following sub-steps:
 (b.1) acidifying said alginate microemulsion with an acidic agent;
 (b.2) mixing additional methylene chloride into the alginate microemulsion; and
 (b.3) washing the aqueous phase with methylene chloride and ethanol to remove surfactant, oil inclusions and methylene chloride.

According to the preferred embodiment of the present invention, the aqueous phase semisolid form alginate is treated to accomplish ionic crosslinking, and afterwards, to be harvested with a colloidal solution form. As a result, the step (c) further comprises the following sub-steps:
 (c.1) dispersing the semisolid form of alginate nanocapsules in acidic solution with sonication and addition of $CaCl_2$ solution to generate calcium alginate nanocapsules;
 (c.2) adding slowly NaOH solution into the calcium alginate nanocapsules to adjust pH to 7.4-7.8 to accomplish ionic crosslinking;
 (c.3) dispersing the calcium alginate nanocapsules in ethanol;
 (c.4) centrifuging the calcium alginate nanocapsules to remove liquid; and
 (c.5) harvesting colloidal solution of the calcium alginate nanocapsules.

That is to say, in the step (c), the alginate nanocapsules of semisolid form is dispersed in 0.5% (v/v, pH3) acetic acid solution with the help of sonication, followed by a slow addition of $CaCl_2$ solution. NaOH solution is then added slowly to adjust pH to 7.4-7.8 to accomplish ionic crosslinking. Finally, the calcium alginate nanocapsules formed is dispersed in ethanol and centrifuged to remove liquid. After ethanol washing, the nanocapsules are dispersed in 142 mM saline (pH 7.4, containing 2 mM $CaCl_2$ and 10 mM HEPES) to form a colloidal solution, which is examined and characterized by PCS analyzer and Atomic Force (AF).

Based on above mentioned method, the following examples are carried out for further demonstration in the present invention.

Example 1

Generation of Ca Alginate Nanocapsules

1. Dissolve 200 mg non-ionic surfactant Span 65 in 8.8 ml of methylene chloride in a 50 ml polypropylene centrifuge tube. Add 1 ml of 1% (w/v) Na alginate solution (10 mM HEPES, pH 7.4). With gentle mixing and inversion, add paraffin oil to adjust the density of oil phase until it becomes balanced with that of aqueous phase.

2. On an ice bath, sonicate to form a w/o microemulsion.

3. With continued sonication, add 630 µl glacial acetic acid dropwisely.

4. Add 10 ml of methylene chloride and mix well. Centrifuge the mixture for 15 minutes at 1,600 rpm. Transfer the aqueous phase containing alginate nanocapsules in a semisolid form to a new tube.

5. Disperse the alginate nanocapsules in 15 ml of 0.5% (v/v) acetic acid. Under continued sonication, add 2 ml of 20 mM calcium chloride into the dispersion. Under a stirred condition, use 1.5 N and 0.5 N NaOH to adjust pH to the range of 7.4-7.8. Add 10 ml of ethanol, mix and remove liquid after centrifugation.

6. Disperse capsules in 15 ml of ethanol by sonication and remove liquid after centrifugation.

7. Disperse capsules in 15 ml of 142 mM saline (pH 7.4, containing 2 mM $CaCl_2$ and 10 mM HEPES) by sonication.

Figure 2:
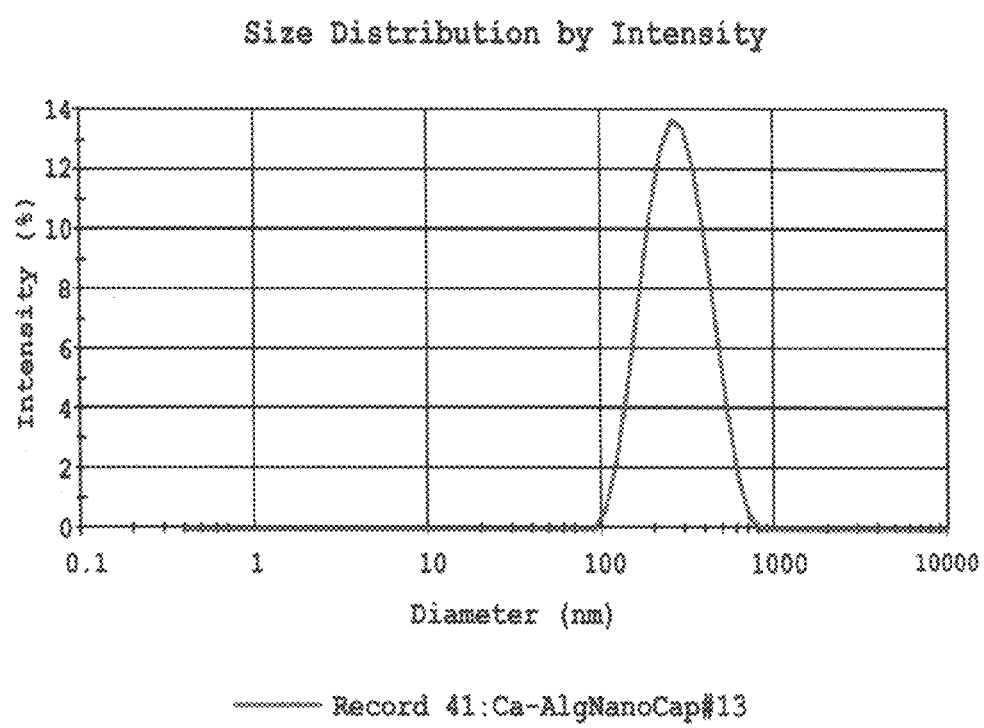
FIG. 2 is schematic view illustrating the size distribution of alginate nanocapsules prepared by the method according to the above preferred embodiment of the present invention.
Figure 3:
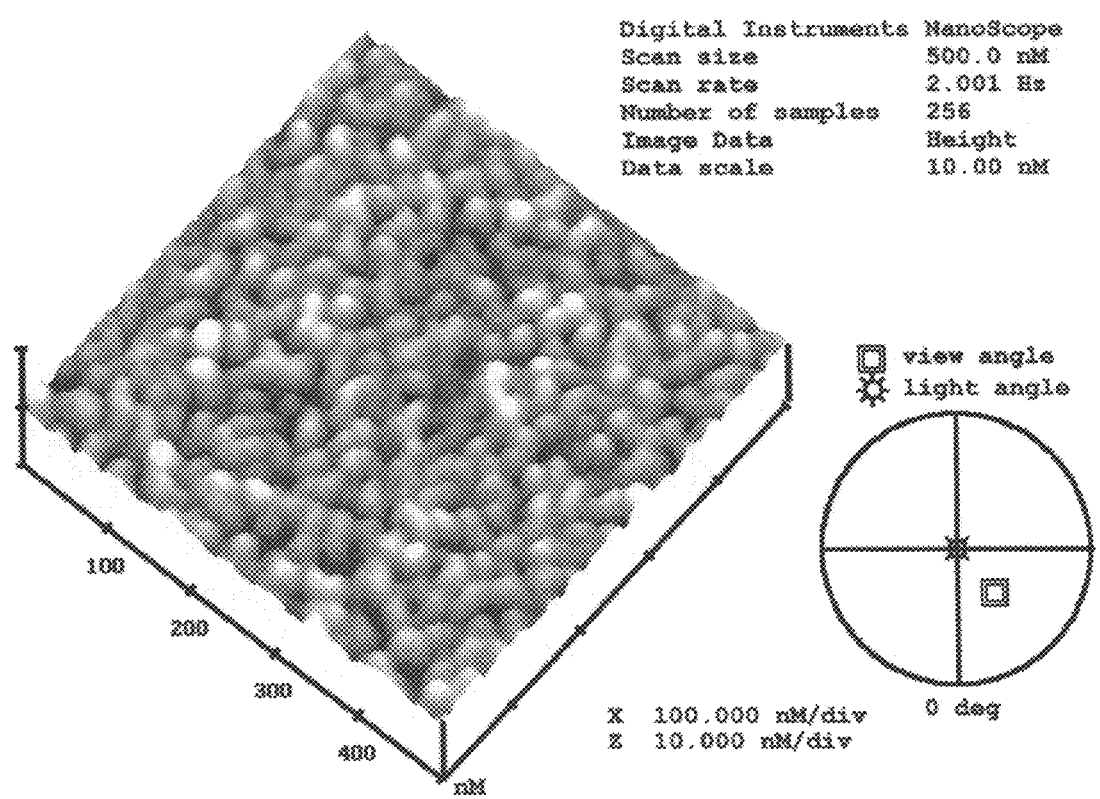
FIG. 3 is schematic view of atomic force microscopy (AFM) of alginate nanocapsules prepared by the method according to the above preferred embodiment of the present invention.

Referring to FIG. 2, the size distribution by intensity according to the above example 1 is illustrated. It is clearly seen that the nanocapsules peaked at intensity 13% with a size range between 100-1,000 nm.

The method according to the preferred embodiment of the present invention, the above mentioned process further comprises a step for preparing covalently crosslinked alginate nanocapsules. That is to say, the alginate nanocapsules thus prepared as above are covalently crosslinked via chemical reactions, such as EDAC/NHS with crosslinkers e.g. ethylene diamine (EDA), and diaminoheptane (DAH), which react with the carboxyl groups on alginate. The covalently crosslinked alginate nanocapsules will exhibit independence of $Ca^{2+}$ and $Ba^{2+}$ for their integrity.

Alginate nanocapsules are washed in 25 mM MES solution (20 mM $CaCl_2$ and 108 mM NaCl, pH 6.5). Diamines, preferably ethylene diamine (EDA), EDAC and NHS are dissolved in MES solutions and added to the capsules, and reacted for about 20 hours. The crosslinked capsules are examined under fluorescent microscope after another EDAC/NHS mediated coupling of fluorescent label AMCA and treatment of critic acid solution to remove $Ca^{2+}$ and $Ba^{2+}$.

On the other hand, the above method could be employed to prepare Ba/Ca Alginate nanocapsules as shown in following example.

Example 2

Generation of Ba/Ca Alginate Nanocapsules

1. In two 50 ml polypropylene tubes (with caps), weigh 400 mg each non-ionic surfactant Span 65 and dissolve in 16.6 ml of methylene chloride. Add 2 ml of Na alginate solution (10 mM HEPES, pH 7.4) and 2 ml of 100 mM $BaCl_2$ (WFI, pH 5.4-5.6) solution in separate tubes. Add paraffin oil to adjust the density of oil phase until the aqueous phase and oil phase are balanced.

2. On ice, sonicate the $BaCl_2$ in methylene chloride and mineral oil into microemulsion (w/o) for 4 minutes at level 11-12 (¼ inch probe, Misonic). And then transfer the emulsion into a stirred beaker.

3. On ice, sonicate the alginate in methylene chloride and mineral oil into emulsion (w/o) for 4 minutes at level 11-12 (¼ inch probe, Misonic). Mix it with the $BaCl_2$ emulsion (w/o) and react for 5 minutes.

4. Aliquot the mixture into four polypropylene tubes, add methylene chloride to about 50 ml, mix and centrifuge for 10 minutes at 1,700 rpm. Separate the gelled alginate from oil phase and pooled into a 50 ml centrifuge tube.

5. Add 100% ethanol, sonicate and spin down alginate capsules. Remove ethanol.

6. Add 16 ml methylene chloride and sonicate to disperse the capsules. Add 32 ml of methylene chloride, mix and centrifuge for 5 minutes at 1,700 rpm. Remove the solvent.

7. Repeat step 6.

8. Add 16 ml ethanol and sonicate to disperse the capsules. Add 32 ml of ethanol, mix and centrifuge for 5 minutes at 1,700 rpm. Remove the solvent.

9. Add 10 ml of 2 mM $CaCl_2$ solution and sonicate to disperse the capsules. Then add 40 ml of 120 mM $CaCl_2$ solution. Mix and centrifuge for 5 minutes at 1,700 rpm. Remove the liquid.

10. Suspend the capsules in 25 ml of 2 mM $CaCl_2$ solution. Examine the capsules under microscope for size evaluation. Add equal volume of ethanol for preservation.

Or otherwise, the calcium alginate nanocapsules could be prepared via above mentioned ionic crosslinking method.

Example 3

Generation of Ca Alginate Nanocapsules

1. In two 50 ml polypropylene tubes, weigh 400 mg each non-ionic surfactant Span 65 and dissolve in 16.6 ml of methylene chloride. Add 2 ml of Na alginate solution (10 mM HEPES, pH 7.4) and 2 ml of 120 mM $CaCl_2$ solution (10 mM HEPES, pH 7.4) solution in separate tubes. Add paraffin oil to adjust the density of oil phase until the aqueous phase and oil phase are balanced.

2. On ice, sonicate the $CaCl_2$ in methylene chloride into microemulsion (w/o) for 4 minutes at level 11-12 (¼ inch probe, Misonic) and then transfer the emulsion into a stirred beaker.

3. On ice, sonicate the alginate, methylene chloride into microemulsion (w/o) for 4 minutes at level 11-12 (¼ inch probe, Misonic). Mix it with the $CaCl_2$ emulsion (w/o) and react for 5 minutes.

4. Aliquot the mixture into four polypropylene tubes, add methylene chloride to about 50 ml, mix and centrifuge for 10 minutes at 1,700 rpm. Separate the gelled alginate from oil phase and pooled into a 50 ml centrifuge tube.

5. Add 100% ethanol, sonicate and spin down alginate capsules. Remove ethanol.

6. Add 16 ml methylene chloride and sonicate to disperse the capsules. Add 32 ml of methylene chloride, mix and centrifuge for 5 minutes at 1,700 rpm. Remove the solvent.

7. Repeat step 6.

8. Add 16 ml ethanol and sonicate to disperse the capsules. Add 32 ml of ethanol, mix and centrifuge for 5 minutes at 1,700 rpm. Remove the solvent.

9. Add 10 ml of 2 mM $CaCl_2$ solution. Examine the capsules under microscope for size evaluation. Add equal volume of ethanol for preservation.

There are two kinds of function groups in abundance in alginate, carboxyl and hydroxyl groups. A crosslinking reaction between the carboxyl groups on the polysaccharides and the amino groups of diamine molecules, mediated by the water soluble condensing reagent 1-ethyl-3-(3-dimethylaminopropyl) carbodiimide (EDAC), enhances the physical structure of the nanocapsules. The nanocapsules thus treated become resistant to the treatment of EDTA or citric acid.

These two kinds of alginate nanocapsules (ionically crosslinked and covalenyly crosslinked) are cleaned to remove the organic solvents and surfactant in order to be biologically compatible and formulated for intravenous applications.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of preparing alginate nanocapsules for intravascular, muscular, oral and subcutaneous delivery of drugs of low molecular weight and macromolecules to deliver therapeutic effects and induce immunological responses towards selected antigens, comprising the following steps:
   a) adding alginate solution into methylene chloride containing a surfactant to form an alginate micro emulsion;
   b) preparing semisolid form alginate nanocapsules by:
      (b.1) acidifying said alginate micro emulsion with an acidic agent to render alginate molecules insoluble to form the semisolid form alginate nanocapsules;
      (b.2) mixing additional methylene chloride into the alginate micro emulsion; and
      (b.3) washing the aqueous phase with methylene chloride and ethanol to remove the surfactant, oil inclusions and methylene chloride; and
      (b4) centrifuging said alginate micro emulsion to separate aqueous phase semisolid form alginate nanocapsules and an oil phase; and
   c) crosslinking said semisolid form nanocapsules to obtain crosslinked alginate nanocapsules, wherein step (c) further comprises the following sub-steps:
      (c.1) dispersing said semisolid form of alginate nanocapsules in acidic solution of pH 3 with sonication and addition of $CaCl_2$ solution to generate calcium alginate nanocapsules;
      (c.2) adding slowly NaOH solution into the calcium alginate nanocapsules to adjust pH to 7.4-7.8 to accomplish ionic crosslinking;
      (c.3) dispersing the calcium alginate nanocapsules in ethanol;
      (c.4) centrifuging the calcium alginate nanocapsules to remove liquid; and
      (c.5) harvesting colloidal solution of the calcium alginate nanocapsules.

2. The method, as recited in claim 1, wherein said alginate microemulsion is prepared with water-in-oil microemulsion.

3. The method, as recited in claim 1, wherein said acidic agent is both soluble in said oil phase and able to partition and dissociate in said aqueous phase.

4. The method, as recited in claim 1, wherein said acidic solution comprises multiple cations by a gradual increase in pH.

5. The method, as recited in claim 2, wherein said alginate capsules are spherical and discrete, with a size of 100-1,000 nanometer in diameter.

6. The method, as recited in claim 1, wherein said alginate capsules are spherical and discrete, with a size of 100-1,000 nanometer in diameter.

7. A method of preparing alginate nanoparticles, comprising:
   adding a 1% (w/v) aqueous sodium alginate solution to methylene chloride containing a nonionic surfactant, with gentle shaking and inversion, to form a mixture;
   adding mineral oil to the mixture until densities are balanced between aqueous and oil phases of the mixture;
   sonicating the mixture to form an alginate micro emulsion;
   acidifying the alginate micro emulsion with an acidic agent to render alginate molecules insoluble to form semisolid alginate nanocapsules;
   mixing additional methylene chloride into the alginate micro emulsion;
   separating the aqueous phase from the oil phase;
   washing the aqueous phase with methylene chloride and ethanol to remove the surfactant, oil inclusions and methylene chloride;
   dispersing semisolid alginate nanocapsules of the aqueous phase into an acidic solution of pH 3 by sonication;
   adding a $CaCl_2$ solution to the alginate nanocapsules in the acidic solution to generate calcium alginate nanocapsules;
   adjusting the pH of the calcium alginate nanocapsules to 7.4-7.8 with NaOH to cause ionic cross linking of the calcium alginate nanocapsules to cause the alginate to gel;
   dispersing the calcium alginate nanocapsules in ethanol;
   centrifuging the calcium alginate nanocapsules to remove liquid; and
   harvesting a colloidal solution of the calcium alginate nanocapsules.

8. The method claim 7, wherein the alginate microemulsion is prepared with a water-in-oil microemulsion.

9. The method claim 7, wherein the alginate capsules are spherical and discrete, with a size of 100-1,000 nanometer in diameter.

10. The method of claim 7, wherein the aqueous sodium alginate solution comprises 10 mM HEPES at pH 7.4.

11. The method claim 7, wherein the sonicating step is performed on an ice bath.

* * * * *